United States Patent
Ozaki et al.

(10) Patent No.: US 10,274,723 B2
(45) Date of Patent: Apr. 30, 2019

(54) VARIABLE SHAPE MIRROR, OPHTHALMOLOGICAL APPARATUS, ADAPTIVE OPTICAL SYSTEM AND METHOD OF MANUFACTURING VARIABLE SHAPE MIRROR

(71) Applicant: CANON KABUSHIKI KAISHA, Tokyo (JP)

(72) Inventors: Hiroyuki Ozaki, Yokohama (JP); Kenji Tamamori, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 266 days.

(21) Appl. No.: 14/749,975

(22) Filed: Jun. 25, 2015

(65) Prior Publication Data

US 2016/0004069 A1    Jan. 7, 2016

(30) Foreign Application Priority Data

Jul. 7, 2014   (JP) .................................. 2014-140088

(51) Int. Cl.
 G02B 26/08      (2006.01)
 A61B 3/14       (2006.01)
 A61B 3/10       (2006.01)

(52) U.S. Cl.
 CPC ........ G02B 26/0841 (2013.01); A61B 3/1025 (2013.01); A61B 3/14 (2013.01)

(58) Field of Classification Search
 CPC .............................. G02B 26/0841; A61B 3/14
 USPC ........................................................ 359/224
 See application file for complete search history.

(56) References Cited

U.S. PATENT DOCUMENTS

| 6,384,952 B1 | 5/2002 | Clark et al. |
| 9,468,376 B2 | 10/2016 | Shimada et al. |
| 2002/0030890 A1 | 3/2002 | Kato et al. |
| 2014/0118695 A1 | 5/2014 | Shimada et al. |
| 2014/0125950 A1 | 5/2014 | Shimada et al. |
| 2014/0362460 A1 | 12/2014 | Nozu et al. |

FOREIGN PATENT DOCUMENTS

| CN | 103784116 A | 5/2014 |
| CN | 103809286 A | 5/2014 |
| JP | 2013-148707 A | 8/2013 |
| WO | 2013/108584 A1 | 7/2013 |

OTHER PUBLICATIONS

Jun. 2, 2017 Chinese Official Action in Chinese Patent Appln. No. 201510381234.X.

*Primary Examiner* — Jack Dinh
(74) *Attorney, Agent, or Firm* — Venable LLP

(57) ABSTRACT

Provided is a technology that realizes a variable shape mirror using an actuator having a comb electrode structure, which can be relatively easily manufactured and displaced in two (±) directions perpendicular to a mirror reference plane. A variable shape mirror (100) includes: a mirror base (111) including a reflective surface (110); and an actuator (101) including a first actuator and a second actuator. Each of the plurality of actuators is connected to the mirror base via a connecting portion (121). The first actuator has a first electrode pair (104, 105) of a comb electrode structure for displacing the connecting portion in a first direction perpendicular to the reflective surface. The second actuator has a second electrode pair (108, 109) of a comb electrode structure for displacing the connecting portion in a second direction opposite to the first direction, the second electrode pair being separately formed from the first electrode pair.

12 Claims, 8 Drawing Sheets

FIRST COMB STRUCTURE

FIRST COMB STRUCTURE

SECOND COMB STRUCTURE

SECOND COMB STRUCTURE

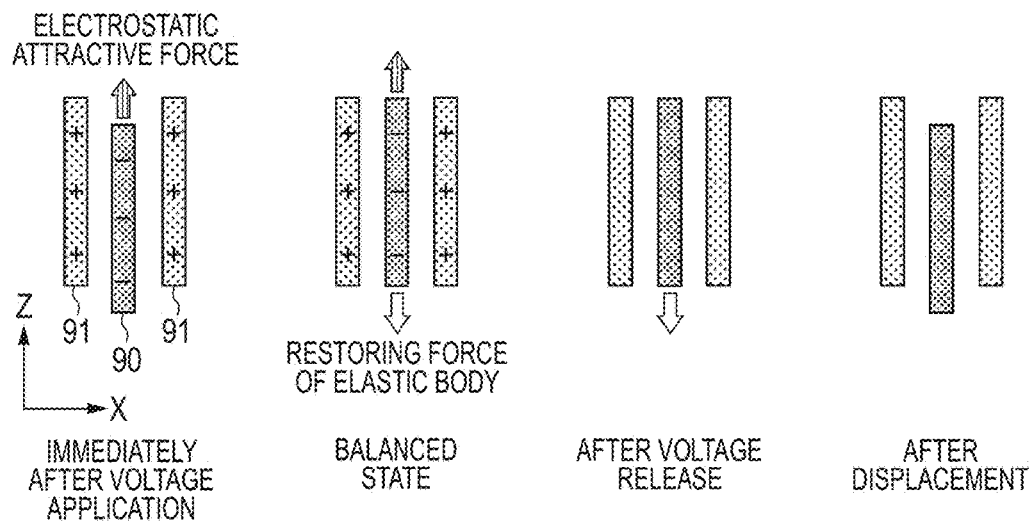
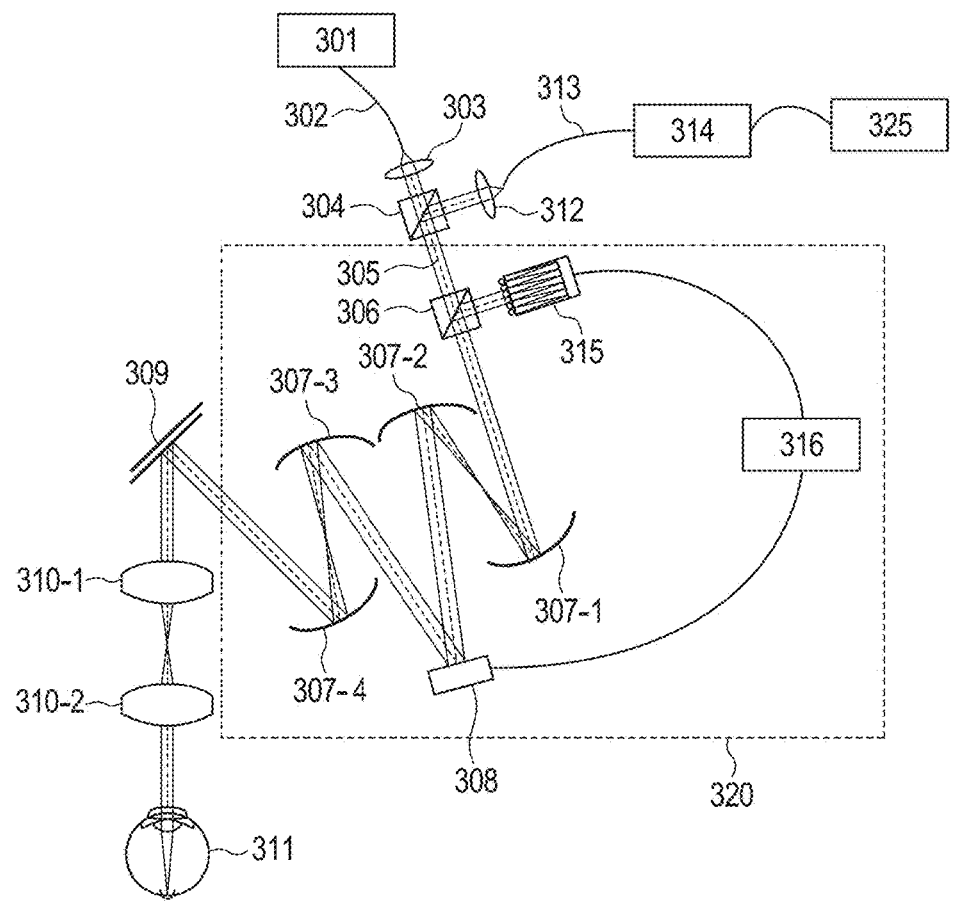

VARIABLE SHAPE MIRROR, OPHTHALMOLOGICAL APPARATUS, ADAPTIVE OPTICAL SYSTEM AND METHOD OF MANUFACTURING VARIABLE SHAPE MIRROR

BACKGROUND OF THE INVENTION

Field of the Invention

The present invention relates to a variable shape mirror, an apparatus such as an adaptive optics system using the same, and a method of manufacturing the same.

Description of the Related Art

A movable mirror and a variable shape mirror of a type to be displaced by an electrostatic attractive force are expected to be applied to various fields utilizing light. For example, the movable mirror and the variable shape mirror each can be utilized as an adaptive optics wavefront correction device to be installed in a fundus inspection apparatus, an astronomical telescope, or the like. As a representative example of such a movable mirror whose reflective surface is displaced by an electrostatic attractive force, there is known a measure of enabling movement by using two parallel plate electrodes, but this parallel plate type has a disadvantage in that the moving amount is small and the displacing direction is one direction that is perpendicular to the reflective surface.

In contrast, in recent years, a variable shape mirror that uses a comb electrode structure and can achieve a larger moving amount has been proposed. An example thereof is disclosed in U.S. Pat. No. 6,384,952. As illustrated in FIG. 10, in a variable shape mirror 500, a support portion 530 that supports a comb electrode 520 on a movable side and a support portion 570 that supports a comb electrode 510 on a fixed side are respectively located in the drawing sheet on upper and lower sides in a perpendicular direction. The movable comb electrode and the fixed comb electrode are opposed to each other, and are arranged so as to be alternately arrayed with a distance. With this, an electrode overlapping area larger than that in the parallel plate type can be achieved. Therefore, a larger electrostatic attractive force can be generated between the comb electrodes, and thus a moving amount of a connecting portion 540 connected to a reflective portion 550 can be increased.

Further, in Japanese Patent Application Laid-Open No. 2013-148707, there is disclosed an exemplary structure of displacement in two directions perpendicular to a reflective surface. As illustrated in FIG. 11A and FIG. 11B, in this variable shape mirror, both a movable comb electrode 1001 and a fixed comb electrode 1002 are electrically divided in a Z direction. Therefore, even when the two electrodes are at the same level, non-overlapping parts are made by applying a voltage, and a displacement force in two directions perpendicular to a reflective portion 903 (±Z directions) can be applied to a movable portion 1003.

In the above-mentioned related-art variable shape mirror of an electrostatic vertical comb electrode type having the structure disclosed in U.S. Pat. No. 6,384,952 illustrated in FIG. 10, when the mirror is driven, displacement occurs in one direction perpendicular to the reflective surface. Specifically, in this variable shape mirror, when an electrostatic actuator is driven, the mirror is displaced only in one direction that extends toward the actuator side and is perpendicular to a reference plane (on the −Z direction side), provided that the a reference plane is at a level of the mirror when the actuator is not driven with no voltage applied thereto. When the mirror is used as an adaptive optics wavefront correction device or the like, if the direction is limited to only one, a large movable amount and a large drive voltage are sometimes necessary for reducing a residual aberration. A structure is thus required in which, in addition to the related-art driving direction, driving in an opposite direction is possible.

Meanwhile, in the above-mentioned example in Japanese Patent Application Laid-Open No. 2013-148707 illustrated in FIG. 11A and FIG. 11B, the displacement force can be applied in the two directions perpendicular to the reflective portion 903. However, the movable comb electrode 1001 and the fixed comb electrode 1002 are electrically divided in the Z direction, which complicates the structure and makes it difficult to manufacture the structure. Further, it is necessary to apply different voltages to upper and lower electrode portions of the movable comb electrode 1001, respectively using a spring 1004, and thus, the spring 1004 has at least three layers and stiffness of the spring 1004 tends to become higher. Therefore, a force generated for the purpose of obtaining a movable amount necessary for the movable portion 1003 and the reflective portion 903 becomes stronger, and the drive voltage tends to become larger.

SUMMARY OF THE INVENTION

The present invention has been made in view of the problems described above, and an object of the present invention is to provide a variable shape mirror that uses an actuator having a comb electrode structure in which, when the mirror is driven, displacement can occur in two directions perpendicular to a reflective surface, and that is relatively easily manufactured.

A variable shape mirror according to one embodiment of the present invention for solving the problems described above adopts the following structure. That is, the variable shape mirror includes: a mirror base including a reflective surface; and an actuator including a connecting portion to be connected to the mirror base, a first actuator, and a second actuator. Further, each of the plurality of actuators is connected to the mirror base via the connecting portion, the first actuator includes a first electrode pair of a comb electrode structure for displacing the connecting portion in a first direction perpendicular to the reflective surface, and the second actuator includes a second electrode pair of a comb electrode structure for displacing the connecting portion in a second direction opposite to the first direction, the second electrode pair being separately formed from the first electrode pair.

Further features of the present invention will become apparent from the following description of exemplary embodiments with reference to the attached drawings.

BRIEF DESCRIPTION OF THE DRAWINGS

FIGS. 8A, 8B, 8C and 8D are sectional views for illustrating a method of driving an actuator having an electrostatic comb electrode structure according to the present invention.

FIG. 9 is a schematic view of an adaptive optics system and an ophthalmological apparatus using the same according to the present invention.

DESCRIPTION OF THE EMBODIMENTS

Figure 1:
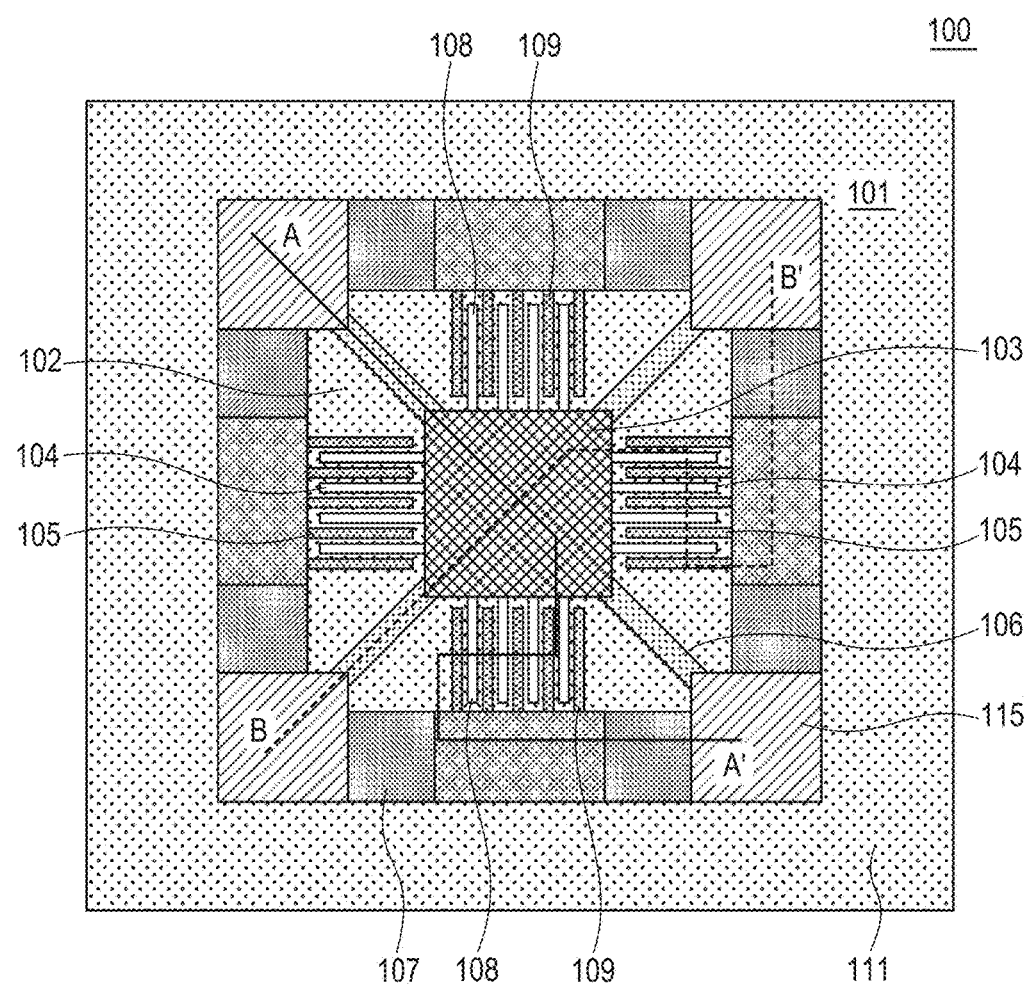
FIG. 1 is a top view for illustrating a variable shape mirror according to an embodiment of the present invention.

Preferred embodiments of the present invention will now be described in detail in accordance with the accompanying drawings.

According to the present invention, in order that a mirror surface (reflective surface) can be displaced in two directions perpendicular to a mirror reference plane, an actuator for displacing the mirror surface includes a first actuator and a second actuator. The first actuator has a first electrode pair of a comb electrode structure formed so as to displace a connecting portion connected to a mirror base in a first direction perpendicular to a reflective surface of the mirror base. The second actuator has a second electrode pair of a comb electrode structure formed separately from the first electrode pair so as to displace the connecting portion in a second direction opposite to the first direction. The first actuator and the second actuator, which are to displace the connecting portion in opposite directions, cannot be simultaneously driven and is required to be selectively driven. A typical example of the actuator is as follows. Each of the first actuator and the second actuator includes a movable comb electrode extending in a direction along the reflective surface from a movable portion leading to the connecting portion, a fixed comb electrode engaged with the movable comb electrode with a gap therebetween, a support portion for supporting the fixed comb electrode, and an elastic member connected to the support portion and to the movable portion. The movable portion of the first actuator and the movable portion of the second actuator are the same common movable portion, and the common movable portion and the connecting portion are connected to each other so as to be integrally displaced. This example is described in detail with regard to Embodiment 1 and Example 1 below. Another typical example of the actuator is as follows. In this case, the first actuator and the second actuator are formed so as to be vertically shifted from each other in a direction perpendicular to the reflective surface, and the movable portion of the first actuator is a first movable portion and the movable portion of the second actuator is a second movable portion different from the first movable portion. More specifically, the first actuator includes a movable comb electrode extending in a direction along the reflective surface from the first movable portion leading to the connecting portion, the fixed comb electrode engaged with the movable comb electrode with a gap therebetween, the support portion for supporting the fixed comb electrode, and an elastic member for connecting the support portion and the first movable portion. The second actuator has a similar structure except that, instead the first movable portion, the second movable portion is included. This example is described in detail with regard to Embodiment 2 below.

In the following, more specific structures are described as embodiments and an example below, but it goes without saying that the present invention is not limited thereto. Various variations and modifications may be made within a range that does not depart from the gist of the present invention.

(Embodiment 1)

Figure 2A:
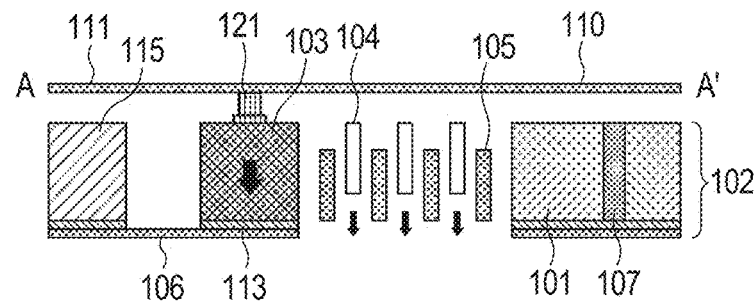
FIGS. 2A and 2B are sectional views for illustrating a method of driving the variable shape mirror of FIG. 1.
Figure 2B:
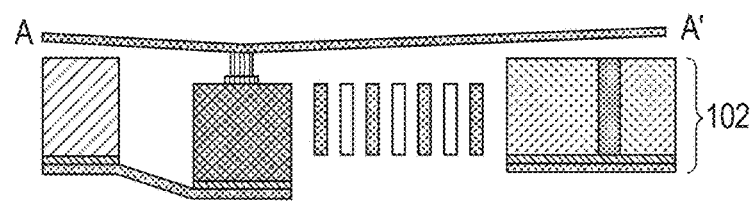
Figure 3A:
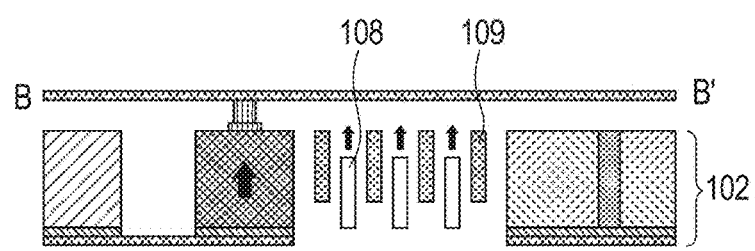
FIGS. 3A and 3B are sectional views for illustrating another method of driving the variable shape mirror of FIG. 1.
Figure 3B:
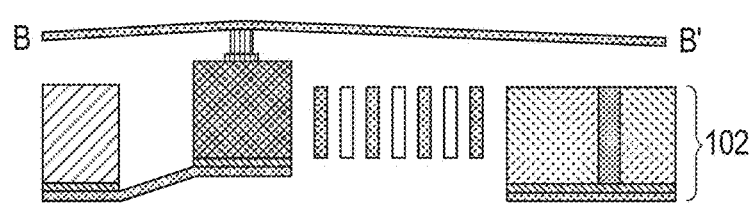

A variable shape mirror 100 of Embodiment 1 according to the present invention is described with reference to FIG. 1, FIG. 2A, FIG. 2B, FIG. 3A, and FIG. 3B. FIG. 1 is a top view of the variable shape mirror 100 of this embodiment. FIG. 2A and FIG. 2B are sectional views taken along the line A-A' of a first electrode pair having a comb structure of the variable shape mirror 100 of this embodiment in two different states. FIG. 3A and FIG. 3B are sectional views taken along the line B-B' of a second electrode pair having a comb structure of the variable shape mirror 100 of this embodiment in two different states. An actuator 101 is formed through processing of a substrate 102. A movable portion 103 is supported by support members 115 through four or more elastic bodies (elastic members) 106. In this case, the elastic bodies 106 each in the shape of a leaf spring are equiangularly arranged about the movable portion 103 having a section in a rotationally symmetrical shape such as a square. This secures stable vertical movement of the movable portion 103 in the direction perpendicular to the plane of FIG. 1.

Each of first movable comb electrodes 104 and second movable comb electrodes 108 extends from the movable portion 103 in a direction in parallel with a surface of the substrate 102. Each of first fixed comb electrodes 105 and second fixed comb electrodes 109 all fixed to the support members 115 via insulating portions 107 extends in a direction in parallel with an upper surface of the support member 115. The first movable comb electrode 104 and the first fixed comb electrode 105 are arranged so as to be opposed to each other, and are arranged so that comb teeth thereof are alternately arrayed with a distance. The second movable comb electrode 108 and the second fixed comb electrode 109 are arranged in a similar relationship. The first movable comb electrode 104 and the first fixed comb electrode 105 form the first electrode pair of the first actuator. The second movable comb electrode 108 and the second fixed comb electrode 109 form the second electrode pair of the second actuator. In this case, there are two first electrode pairs and two second electrode pairs. The two electrode pairs are arranged so as to be 180° rotationally symmetric with each other with the movable portion 103 therebetween. A plurality of electrode pairs can be arranged. In that case, it is preferred that the plurality of electrode pairs be equiangularly arranged about the movable portion 103. This structure also secures stable vertical movement of the movable portion 103 in the direction perpendicular to the plane of FIG. 1.

Next, operation of the actuator 101 including the first actuator and the second actuator and of the variable shape mirror 100 are described with reference to FIG. 2A, FIG. 2B, FIG. 3A, and FIG. 3B. There is a level difference in a direction perpendicular to an upper surface of the support member 115 between each of the two pairs of the first movable comb electrode 104 and the first fixed comb electrode 105. In other words, the movable comb electrode and the fixed comb electrode have non-overlapping parts in the direction perpendicular to the upper surface of the support member 115. This is because this embodiment employs a method utilizing a phenomenon that a force acts and displacement occurs in an overlapping direction when the comb electrodes are attracted to each other due to an electrostatic attractive force (variable overlapping type). In this phenomenon, no further displacement occurs when the comb electrodes are entirely overlapped with each other, and hence, it is required that, in an initial position, a size of an overlapping part be reduced so that the size of the overlapping part is increased when a voltage is applied. The first movable comb electrode 104 and the first fixed comb electrode 105 are electrically insulated from each other. By applying a voltage between the first movable comb electrode 104 and the first fixed comb electrode 105, the movable portion 103 is displaced in the direction perpendicular to the upper surface of the support member 115 under a state in which the distance between the electrodes 104 and 105 is maintained. An electrostatic attractive force Fz in a Z direction that acts when a potential difference is applied between the first movable comb electrode 104 and the first fixed comb electrode 105 is represented by Expression (1).

$$Fz=[(\varepsilon_0 \cdot N \cdot h)/(2g)] \cdot (Vm-Vf)^2 \qquad (1)$$

where $\varepsilon_0$ represents a permittivity of vacuum, N represents the number of gaps between the comb electrodes, h represents an overlapping length between the movable comb electrode and the fixed comb electrode, Vm represents a potential of the movable comb electrode, Vf represents a potential of the fixed comb electrode, and g represents a width of the gap between the comb electrodes.

First, as illustrated in FIG. 2A for illustrating a state immediately after a voltage is applied, by applying a potential difference between the first movable comb electrode 104 and the first fixed comb electrode 105, an electrostatic attractive force is generated and the electrodes are attracted to each other. In this way, the first movable comb electrode 104 and the first fixed comb electrode 105 are attracted to each other, but, with regard to a direction in which the comb teeth are opposed to each other, a substantially uniform electrostatic attractive force is applied on right and left sides of the electrodes. Thus, displacement occurs in a −Z direction that is perpendicular to a reflective surface 110.

Then, the state becomes balanced as illustrated in FIG. 2B. Specifically, the first movable comb electrode 104 stops at a position at which a restoring force of the elastic bodies 106 and the electrostatic attractive force that causes displacement of the movable portion 103 are balanced. When the potential difference between the first movable comb electrode 104 and the first fixed comb electrode 105 is set to 0 V, the restoring force of the elastic bodies 106 returns the first movable comb electrode 104 to its initial position.

On the other hand, with regard to each of the two pairs of the second movable comb electrode 108 and the second fixed comb electrode 109 that are illustrated in FIG. 3A and FIG. 3B, a direction in which the second movable comb electrode 108 and the second fixed comb electrode 109 are displaced in the Z direction when no voltage is applied thereto is different from that in the case of the first movable comb electrode 104 and the first fixed comb electrode 105. Therefore, the movable portion 103 can be displaced relatively in a +Z direction that is perpendicular to the reflective surface 110 due to an electrostatic attractive force generated by the voltage applied. In this way, the fixed comb electrodes and the movable comb electrodes are arranged so as to have non-overlapping parts in the direction perpendicular to the upper surface of the support member 115 when a voltage control unit applies no voltage. The actuator 101 includes the first electrode pairs in each of which the movable comb electrode 104 is displaced to the reflective surface 110 side with respect to the fixed comb electrode 105, and the second electrode pairs in each of which the movable comb electrode 108 is displaced to a side opposite to the reflective surface 110 side with respect to the fixed comb electrode 109. Therefore, by selecting a comb electrode to which a voltage is applied from the first electrode pairs and the second electrode pairs, the movable portion 103 can be displaced to the two directions perpendicular to the reflective surface 110 (±Z directions).

Further, according to this embodiment, as illustrated in FIG. 1 to FIG. 3B, even when a voltage is applied between the movable comb electrode and the fixed comb electrode to generate an electrostatic attractive force, and the electrodes are attracted to each other, neither of the comb electrodes collides with a member connected to the other comb electrode.

In the structure disclosed in U.S. Pat. No. 6,384,952 described above, when the movable comb electrodes are displaced, the fixed comb electrodes and the support portions are arranged in the direction perpendicular to the surface of the substrate, which is the moving direction of the movable comb electrode. Therefore, an electrostatic attractive force may be generated between a leading end surface of the movable comb electrode and the support portion surface to cause pull-in when an excessive electrostatic attractive force is generated as compared to the restoring force of the spring, and thus collision may occur between the movable comb electrode and the support portion. However, according to the structure of this embodiment, the support portion is not arranged in the direction perpendicular to the surface of the substrate, which is the moving direction of the movable comb electrode, and hence pull-in does not occur. In other words, with the structure of this embodiment, even when the electrostatic attractive force acts, both of the comb electrodes may pass each other without collision. Therefore, pull-in does not occur, and short-circuit of the electrodes does not occur as well.

On the other hand, in the structure disclosed in the example in Japanese Patent Application Laid-Open No. 2013-148707, by electrically dividing both the movable comb electrode and the fixed comb electrode in the Z direction, displacement in the two directions perpendicular to the reflective surface can be caused. In order to attain this, it is necessary to form an insulating structure for the electrical division in the Z direction of the comb electrodes, which tends to complicate the structure and the manufacturing method therefor. Further, it is necessary to apply different voltages to the upper and lower electrode portions of the comb electrodes through the spring member, and thus, the spring has three or more layers including an insulating layer, which tends to complicate the structure. Still further, in order to obtain a necessary resistance value and necessary insulation, stiffness of the spring member tends to become higher and a force to be generated for the purpose of obtaining a necessary movable amount tends to become stronger. However, according to the structure and operating principle of this embodiment, a complicated structure for electrically dividing the movable comb electrode and the fixed comb electrode is not necessary. Further, the movable portion and the movable comb electrode are the common electrode, and thus, the spring (elastic body) has a simple single-layer structure, which can lower the stiffness of the spring to lower a drive voltage necessary to deform the spring. According to this embodiment, a voltage application unit for applying different voltages to the respective fixed comb electrodes is included, but the common movable portion, the first movable comb electrodes, and the second movable comb electrodes are electrically at the same potential.

Example 1

Example 1 is a more specific mode of the variable shape mirror according to Embodiment 1 described above. The variable shape mirror 100 according to this example is described with reference to FIG. 1, FIG. 2A, and FIG. 2B. In this example, the actuator 101 including the first actuator and the second actuator is formed by processing the substrate 102 made of silicon. The substrate 102 has a thickness of 300 μm to 800 μm for the purpose of inhibiting breakage thereof and the like when processed. The movable portion 103 is supported by the substrate 102 through the four elastic bodies 106. The elastic bodies 106 are each formed by processing an elastic body layer made of silicon, which is formed on the substrate 102 via an insulating layer (BOX layer) 113. Longitudinal directions of the four elastic bodies 106 form angles of 90° therebetween to inhibit rotation of the elastic bodies 106 in unnecessary directions. Each of the first movable comb electrodes 104 and the second movable comb electrodes 108, all extending from the movable portion 103 in a direction in parallel with the surface of the substrate, is formed between end portions of two adjacent elastic bodies 106 formed on the movable portion 103. Each of the first fixed comb electrodes 105 and the second fixed comb electrodes 109 extends in a direction in parallel with the upper surface of the support member 115. The first movable comb electrode 104 and the first fixed comb electrode 105, and the second movable comb electrode 108 and the second fixed comb electrode 109, are arranged so as to be opposed to each other, and are arranged so that comb electrodes thereof are alternately arrayed.

As expressed in Expression (1) above, as the overlapping length h between the movable comb electrode 104 (108) and the fixed comb electrode 105 (109) becomes larger and the gap therebetween becomes smaller, the generated force becomes stronger. It is desired that the movable comb electrode 104 (108) have a length of 300 μm or more and the gap between the movable comb electrode 104 (108) and the fixed comb electrode 105 (109) be 4 μm to 10 μm. The movable comb electrode 104 (108) and the fixed comb electrode 105 (109) are formed by a photolithography process and a dry etching process. Further, the movable comb electrode 104 (108) and the fixed comb electrode 105 (109) that are formed each have a height that is approximately the same as the thickness of the substrate 102, and the height is 300 μm to 800 μm.

The movable comb electrode 104 (108) and the fixed comb electrode 105 (109) are processed so as to have non-overlapping parts in the direction perpendicular to the reflective surface 110 when the voltage control unit applies no voltage. In the first electrode pair, the first movable comb electrode 104 is displaced to the reflective surface 110 side with respect to the first fixed comb electrode 105, and, in the second electrode pair, the second movable comb electrode 108 is displaced to the side opposite to the reflective surface 110 side with respect to the second fixed comb electrode 109. This structure can be manufactured by partly modifying a manufacturing method described in Embodiment 2 below. The method includes, for example, the following steps of: preparing a first substrate including a silicon layer, an insulating layer, and a handle layer; forming, on a second substrate, a plurality of connecting portions and a plurality of actuators each including a first actuator having a first electrode pair of a comb electrode structure and a second actuator having a second electrode pair of a comb electrode structure; bonding together the first substrate and the second substrate via the plurality of connecting portions formed on the second substrate; and removing the handle layer and the insulating layer of the first substrate to form a reflective member.

The first movable comb electrodes 104, the second movable comb electrodes 108, and the movable portion 103 are formed of the same material and are configured to be electrically at the same potential. Therefore, by selecting a fixed comb electrode to which a voltage is to be applied, the movable portion 103 can be displaced to the two directions perpendicular to the surface of the substrate (±Z directions). The structure and operating principle of the actuator 101 are as described above with reference to FIG. 2A, FIG. 2B, FIG. 3A, and FIG. 3B. Further, the amount of displacement between the movable comb electrode 104 (108) and the fixed comb electrode 105 (109) determines a movable region of the actuator including the first actuator and the second actuator, and thus, it is desired that the amount of displacement be 5 μm or more.

Further, by two-dimensionally arranging the plurality of actuators of the actuator 101 and connecting the actuators of the actuator 101 to one reflective member (mirror portion or mirror base) 111 via a connecting portion 121, the variable shape mirror is formed. It is desired that the reflective member 111 have a thickness of 10 μm or less for the purpose of reducing a generated force necessary for deformation thereof. The variable shape mirror 100 of this example can obtain a desired shape by displacing the common movable portion 103 leading to the connecting portion 121 separately by the first actuator or the second actuator. This can change an optical path length of light reflected at a desired position by the reflective member 111, and thus, the variable shape mirror can be used as a wavefront correction device.

In this example, a type that has one continuous reflective member 111 connected to the plurality of actuators of the actuator 101 via the movable portion and the connecting portion is described, but a type in which each of a plurality of actuators of the actuator 101 is connected to one mirror portion via a movable portion and a connecting portion is also possible. This can change an optical path length of light reflected by each of the actuators, and thus, the variable shape mirror can be used as a wavefront correction device.

(Embodiment 2)

Figure 4A:
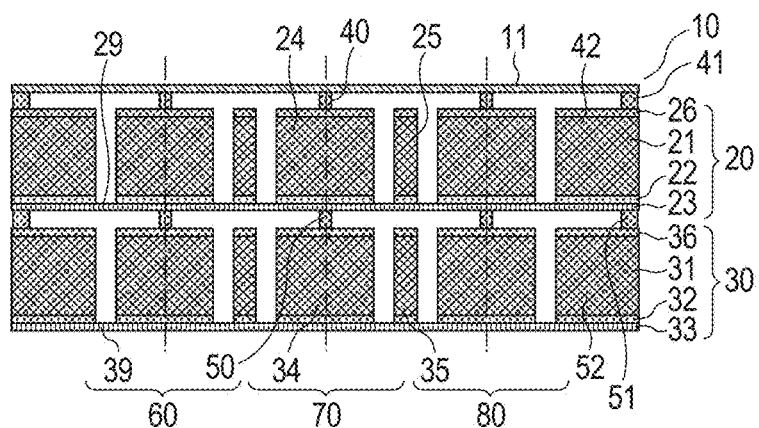
FIGS. 4A, 4B and 4C are sectional views and a plan view for illustrating a variable shape mirror according to another embodiment of the present invention.
Figure 4B:
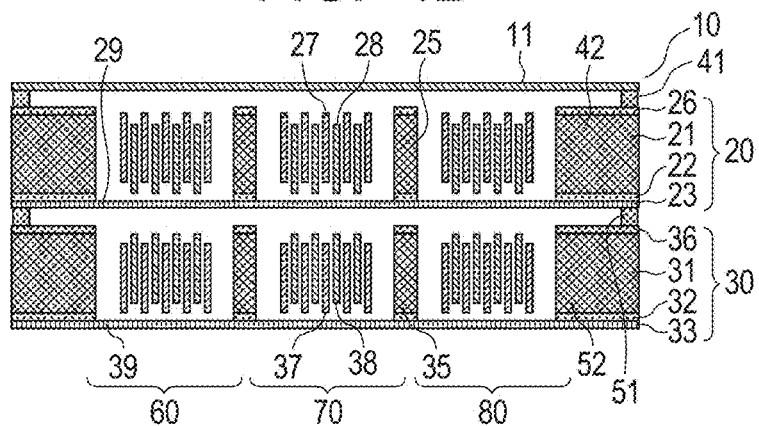
Figure 4C:
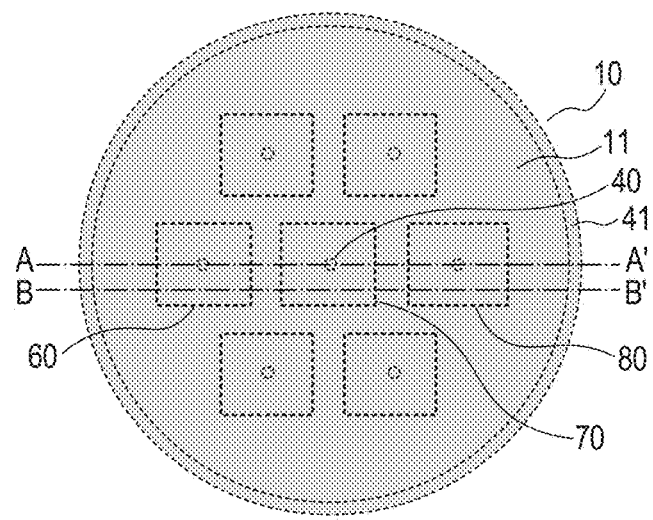

A variable shape mirror 10 of Embodiment 2 according to the present invention is described with reference to FIG. 4A to FIG. 4C and FIG. 5A to FIG. 5E. FIG. 4C is a plan view of the variable shape mirror, and FIG. 4A and FIG. 4B are sectional views taken along the line A-A' and taken along the line B-B', respectively, of the plan view of FIG. 4C. The variable shape mirror 10 includes a mirror portion (mirror base) 11, a first actuator array 20, and a second actuator array 30. The mirror portion 11 is connected to the first actuator array 20 via posts 40 as connecting portions and a circumferential connecting portion 41. The second actuator array 30 is connected to the first actuator array 20 via posts 50 and a circumferential connecting portion 51. Note that, in FIG. 4C, the posts 40 and the circumferential connecting portion 41 are on a rear surface side of the mirror base 11, and thus, are represented by the dotted lines.

The posts 40 are connected to movable portions 24 of the first actuator array 20 via an insulating layer 26. The circumferential connecting portion 41 is connected to a peripheral fixed portion 42 of the first actuator array 20 via the insulating layer 26. The posts 50 are connected to movable portions 34 of the second actuator array 30 via an insulating layer 36. The circumferential connecting portion 51 is connected to a peripheral fixed portion 52 of the second actuator array 30 via the insulating layer 36. In the variable shape mirror 10 illustrated in FIG. 4C, the first actuator array 20 having seven movable portions 24 is connected to one mirror base 11 having a continuous reflective surface. As illustrated in FIG. 4A, seven movable portions 34 of the second actuator array 30 are coaxially connected to rear surfaces of the movable portions 24 of the first actuator array 20, respectively. Alignment precision between the first actuator array 20 and the second actuator array 30 in this coaxial connection is, for example, within ±0.5 µm, and thus, the drive of the actuator in a vertical direction in FIG. 4A (direction perpendicular to the reflective surface) is hardly affected. In other words, displacement in a horizontal direction is hardly caused in the drive in the vertical direction. Note that, in FIG. 4A and FIG. 4B, the first actuator array 20 also includes a silicon handle layer 21, an insulating layer (BOX layer) 22, and a SOI layer 23, and the second actuator array 30 also includes a silicon handle layer 31, an insulating layer (BOX layer) 32, and a SOI layer 33.

The variable shape mirror 10 includes the first actuators and the second actuators, and thus, can be driven in the two (±) directions perpendicular to the mirror reference plane. Specifically, by forming a plurality of actuators each including a first actuator and a second actuator that are vertically shifted and coaxially connected to each other, and connecting the actuators to the mirror base via the connecting portions, the variable shape mirror 10 can be driven in the two (±) directions. This is described in detail in the following with reference to the drawings. As illustrated in FIG. 4A, the first actuator array 20 has a structure in which a fixed portion 25, the peripheral fixed portion 42, and the movable portions 24 are connected through an elastic body 29. An insulating layer (BOX layer) 22 is formed between the elastic body 29 and each of the fixed portion 25, the peripheral fixed portion 42, and the movable portions 24 for electrical insulation therebetween. Further, as illustrated in FIG. 4B, the first actuator array 20 includes movable comb electrodes 27 connected to the movable portions 24, respectively, and fixed comb electrodes 28 fixedly connected to the fixed portion 25. When the first actuator array 20 is not driven, in a direction perpendicular to the mirror surface of the mirror base 11, upper and lower surfaces of the movable comb electrode 27 are positioned to be higher (nearer to the mirror surface) than upper and lower surfaces of the fixed comb electrode 28, respectively.

As illustrated in FIG. 4A, the second actuator array has a structure in which a fixed portion 35, the peripheral fixed portion 52, and the movable portions 34 are connected through an elastic body 39. An insulating layer (BOX layer) 32 is formed between the elastic body 39 and each of the fixed portion 35, the peripheral fixed portion 52, and the movable portions 34 for electrical insulation therebetween. The second actuator array 30 includes movable comb electrodes 37 connected to the movable portions 34, respectively, and fixed comb electrodes 38 fixedly connected to the fixed portion 35. When the second actuator array 30 is not driven, in the direction perpendicular to the mirror surface of the mirror base 11, upper and lower surfaces of the movable comb electrode 37 are positioned to be lower (farther to the mirror surface) than upper and lower surfaces of the fixed comb electrode 38, respectively.

FIG. 8A to FIG. 8D are sectional views for illustrating a method of driving an actuator of an electrostatic comb type according to this embodiment. As a structure of the actuator of an electrostatic comb type, for the sake of simplicity, only a comb tooth of a movable comb electrode 90 and comb teeth of a fixed comb electrode 91 are illustrated. As illustrated in FIG. 8A, immediately after a voltage is applied, the movable comb electrode 90 is displaced to the +Z direction side of directions perpendicular to the substrate (Z directions) by an electrostatic attractive force generated between the comb electrodes with charges of opposite polarities given to the movable comb electrode 90 and the fixed comb electrode 91, respectively. In other words, a movable portion (not shown here) that supports the movable comb electrode 90 can be driven by the electrostatic attractive force generated between the comb electrodes. As described above in Embodiment 1, the electrostatic attractive force causes the movable comb electrode 90 to approach the fixed comb electrode 91, but, with regard to a horizontal direction (X direction), a substantially uniform electrostatic attractive force is applied on left and right sides of the electrode. Thus, displacement occurs only in an upward vertical direction. In a balanced state illustrated in FIG. 8B, an elastic body (not shown here) plays a role in stopping the movable comb electrode 90 at a position at which, when the movable comb electrode 90 is displaced by the electrostatic attractive force, the electrostatic attractive force and the restoring force of the elastic body are balanced. After the voltage is released as illustrated in FIG. 8C, the electrostatic attractive force between the comb electrodes is released to lose the balance between the electrostatic attractive force and the restoring force of the elastic body, and the restoring force of the elastic body acts on the movable comb electrode 90. After the displacement occurs as illustrated in FIG. 8D, the restoring force of the elastic body returns the movable comb electrode 90 to its initial position. The driving method described above is the same as the driving method of Embodiment 1 described above. Note that, the polarities of the voltages applied to the movable comb electrode 90 and the fixed comb electrode 91 (polarities of given charge) may be opposite to those illustrated in FIG. 8A to FIG. 8D. In other words, in this embodiment, displacement of the movable portion is controlled in accordance with voltages applied to the movable comb electrode and the fixed comb electrode, respectively.

The electrostatic attractive force Fz in the Z direction that acts when a potential difference is given between the movable comb electrode and the fixed comb electrode is represented by Expression (1) above. Therefore, in the first actuator array 20, the fixed comb electrodes 28 are grounded and a voltage is applied to the movable comb electrodes 27 connected to the plurality of movable portions 24 via wiring (not shown) individually connected to the movable portions 24, and the plurality of movable portions 24 are individually displaced in the −Z direction opposite to the mirror base side of the directions perpendicular to the mirror reference plane. Further, in the second actuator array 30, the fixed comb electrodes 38 are grounded and a voltage is applied to the movable comb electrodes 37 via wiring (not shown) individually connected to the plurality of movable portions 34, and the plurality of movable portions 34 are individually displaced in the +Z direction on the mirror base side of the directions perpendicular to the mirror reference plane. Therefore, with reference to FIG. 4B that is a sectional view taken along the line B-B', the variable shape mirror 10 includes three actuators 60, 70, and 80 that are driven in the two (±) directions perpendicular to the mirror surface, with the reference plane being a level of the mirror when no voltage is applied thereto. Therefore, in the variable shape mirror 10, in the direction perpendicular to the mirror reference plane, when the mirror portion 11 is to be displaced in the −Z direction, the first actuator array 20 is driven, and when the mirror portion 11 is displaced in the +Z direction, the second actuator array 30 is driven. In this way, the variable shape mirror 10 can be driven in the two (±) directions.

The variable shape mirror according to this embodiment can be driven in the two (±) directions, and thus, compared with a related-art variable shape mirror, a desired mirror shape can be realized with approximately half a driven amount. Note that, in FIG. 4C, a structure is illustrated in which seven actuators are connected to the variable shape mirror portion 11 having a continuous reflective surface, but this is only exemplary. By increasing the number of the actuators, a more complicated mirror surface shape can be realized with precision. Further, the arrangement of the first actuator array and the second actuator array in the direction perpendicular to the mirror surface may be opposite to that described above. Specifically, the second actuator array may be connected to the mirror base 11 and the first actuator array may be connected to a rear surface of the second actuator array.

Further, dimensions of the movable comb electrode and the fixed comb electrode in the first actuator and the second actuator according to this embodiment may be the same or may be different. Further, longitudinal directions of the comb teeth of the first actuator and the second actuator in surfaces in parallel with the mirror surface according to this embodiment may be in parallel with each other, may be orthogonal to each other, or may form an angle. Further, the first actuator and the second actuator according to this embodiment each have an array structure having the same pitch so that the movable portion thereof is coaxially arranged. However, for example, the array pitches of the first actuator may be an integral multiple of the array pitches of the second actuator, and vice versa. For example, a movable portion having pitches that are an integral multiple may laterally extend, but the connecting portions thereon may be arranged in the same way. Further, with regard to a layout of springs (elastic bodies) of the first actuator and the second actuator according to this embodiment seen from a direction perpendicular to the mirror surface, the springs may overlap each other, or may be arranged so as to be point symmetric forming an appropriate angle therebetween. Further, maximum driven amounts of the first actuator and the second actuator according to this embodiment may be the same or may be different. In short, insofar as an intended purpose that a movable portion is driven in the two (±) directions with satisfactory precision is accomplished, the first actuator and the second actuator may be modified in various ways as appropriate.

(Method of Manufacturing Variable Shape Mirror)

Next, a method of manufacturing the variable shape mirror according to this embodiment is described with reference to FIG. 5A to FIG. 5E. FIG. 5A to FIG. 5E are process sectional views taken along the line A-A' of FIG. 4C. In the method of manufacturing the variable shape mirror according to this embodiment, a SOI layer (silicon layer) of a SOI substrate 1 is the mirror base 11 to be transferred onto the actuator including the first actuator array 20 and the second actuator array 30.

Figure 5A:
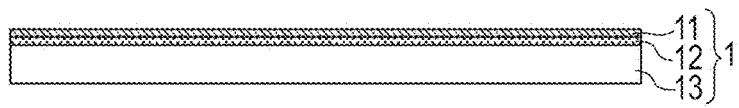
FIGS. 5A, 5B, 5C, 5D and 5E are sectional views for illustrating a method of manufacturing the variable shape mirror of FIG. 4A to FIG. 4C.
Figure 5B:
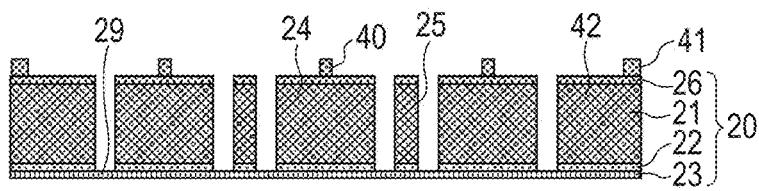

First, as a first substrate including three layers of a silicon layer, an insulating layer, and a handle layer, for example, the SOI substrate 1 is prepared. The SOI substrate 1 includes, for example, a SOI layer 11 made of silicon, a handle layer 13, and a BOX layer (insulating layer) 12 of silicon oxide formed therebetween. Then, as illustrated in FIG. 5B, the first actuator array 20 for deforming the mirror base 11 to the −Z direction side of the directions perpendicular to the mirror reference plane is prepared. The posts 40 serving as connecting portions to the mirror base 11 are formed on the movable portions 24 of the first actuator array 20, and the circumferential connecting portion 41 to be connected to a periphery of the mirror base 11 is formed on the peripheral fixed portion 42.

Figure 5C:
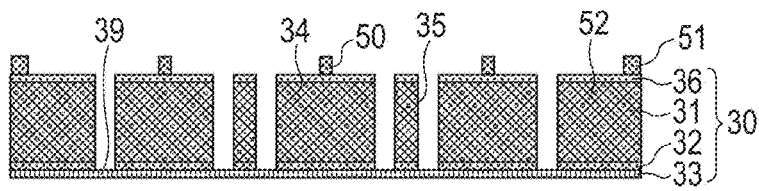

Then, as illustrated in FIG. 5C, the second actuator array 30 for deforming the mirror base 11 to the +Z direction side of the directions perpendicular to the mirror reference plane is prepared. The posts 50 serving as connecting portions to the first actuator array 20 are formed on the movable portions 34 of the second actuator array 30, and the circumferential connecting portion 51 to be connected to the rear surface of the first actuator array 20 is formed on the peripheral fixed portion 52. Then, the first substrate from which the mirror base 11 is formed and the first actuator array 20 are bonded together via the posts 40 and the circumferential connecting portion 41. Then, after that, the substrate of the second actuator array 30 is bonded to the rear surface of the first actuator array 20 via the posts 50 and the circumferential connecting portion 51. This connects the movable portions 24 of the first actuator array 20 and the movable portions 34 of the second actuator array 30 so as to be integrally displaced through functioning of the SOI layers 23 and 33 that are the elastic bodies. Further, the peripheral fixed portion 42 of the first actuator array 20 and the peripheral fixed portion 52 of the second actuator array 30 are integrally fixed to each other.

As the posts 40 and 50 and the circumferential connecting portions 41 and 51, for example, Au bumps are used. In this case, Au pads (not shown) are formed on the mirror base 11 and the rear surface of the substrate of the first actuator array 20. Then, those (the posts 40 and the circumferential connecting portion 41, and the Au pads on the mirror base 11, and, the posts 50 and the circumferential connecting portion 51, and the Au pads on the rear surface of the substrate of the first actuator array 20) are aligned with precision to be bonded together, respectively. In this bonding, for example, Au—Au surface activated bonding is used. In this method, the bonding is performed after the surfaces of the Au bumps and the Au pads are activated by removing organic matters thereof by Ar plasma. Note that, room temperature surface activated bonding is used as the bonding method according to this embodiment, but the present invention is not limited thereto.

In this case, the first substrate from which the mirror base 11 is formed and the substrate of the first actuator array 20 are, when bonded together, aligned with each other by aligning alignment marks M (not shown) formed on the substrate of the first actuator array 20 with alignment marks L (not shown) formed on the first substrate.

Figure 5D:
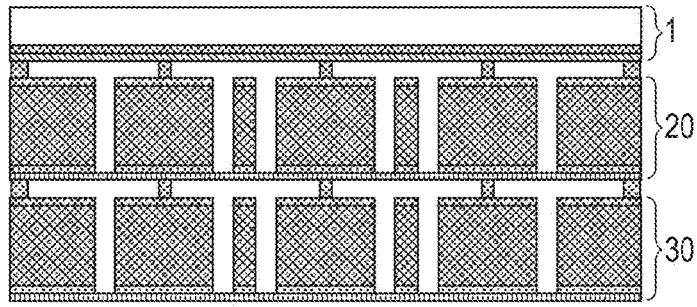

Further, the substrate of the first actuator array 20 and the substrate of the second actuator array 30 are, when bonded together, aligned with each other by aligning alignment marks N (not shown) formed on the substrate of the second actuator array 30 with the alignment marks L (not shown) formed on the first substrate as illustrated in FIG. 5D. The alignment precision in the two kinds of bonding described above can be ±0.5 μm or less, and thus, the plurality of movable portions 24 and 34 can be coaxially arranged, respectively, in a highly precisely aligned state.

Figure 5E:
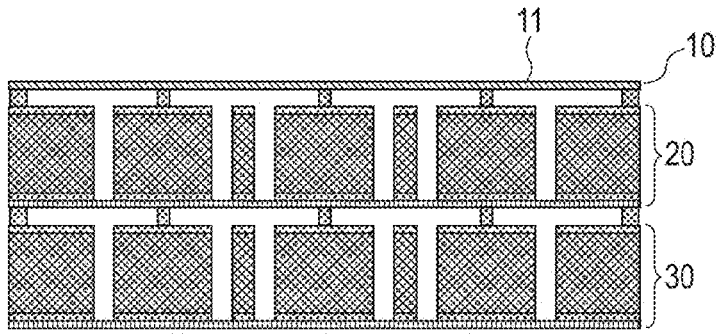

Then, as illustrated in FIG. 5E, the handle layer 13 and the insulating layer (BOX layer) 12 of the SOI substrate 1 as the first substrate are removed. This can form a structure in which the mirror base 11 formed of the SOI layer is connected to the actuator including the first actuator array 20 and the second actuator array 30. The handle layer 13 is removed by, for example, silicon dry etching. An end of the etching is controlled by plasma emission spectroscopy, and the insulating layer (BOX layer) of the SOI substrate 1 is used as an etching stopper layer. In this silicon dry etching, by adopting conditions with which an etching selectivity ratio between the insulating layer (BOX layer) 12 as the etching stopper layer and the handle layer 13 is high, the insulating layer (BOX layer) 12 protects the SOI layer 11, and thus, the SOI layer 11 is not etched. The handle layer 13 may be removed by wet etching using an aqueous solution of tetramethylammonium hydroxide (TMAH) or the like.

Then, the insulating layer (BOX layer) 12 is removed by, for example, wet etching using buffered hydrofluoric acid (BHF). In this case, the SOI layer (mirror base) 11 under the insulating layer (BOX layer) 12 has a high etching selectivity ratio with respect to the insulating layer (BOX layer) 12, and thus, is hardly etched. Therefore, the insulating layer (BOX layer) 12 can be removed without damaging the mirror base 11. The insulating layer (BOX layer) 12 may be removed by, other than this, dry etching using vapor hydrofluoric acid.

Then, a reflectivity of the variable shape mirror 10 may be improved by forming a reflective film on the mirror base 11. The reflective film is made of, for example, Au, and, as an adhesive layer, for example, Ti may be used.

As described above, the method of manufacturing the variable shape mirror according to this embodiment at least includes the following steps: preparing the first substrate including the three layers of the SOI layer, the insulating layer, and the handle layer; forming the plurality of first actuators on the second substrate; and forming the plurality of second actuators on a third substrate. Further, the manufacturing method includes: bonding together the connecting portions in a region of the SOI layer and the first actuator to connect the first substrate and the second substrate; connecting the second substrate and the third substrate; and removing the handle layer and the insulating layer of the first substrate. The method described above can relatively easily form a variable shape mirror having actuators that can be driven in two (±) directions.

(Method of Manufacturing First Actuator Array)

A structure and a manufacturing method of the first actuator array 20 illustrated in FIG. 4A to FIG. 4C that is suitable for the variable shape mirror according to this embodiment are described with reference to FIG. 6A to FIG. 6H. The first actuator array 20 is actuators of an electrostatic comb type, and is for causing displacement to, for example, the −Z direction side of the directions perpendicular to the mirror reference plane. A stroke of the displacement (maximum amount of displacement) is relatively small and is, for example, 20 μm, but there is an advantage that the amount of displacement can be finely controlled.

Figure 6A:
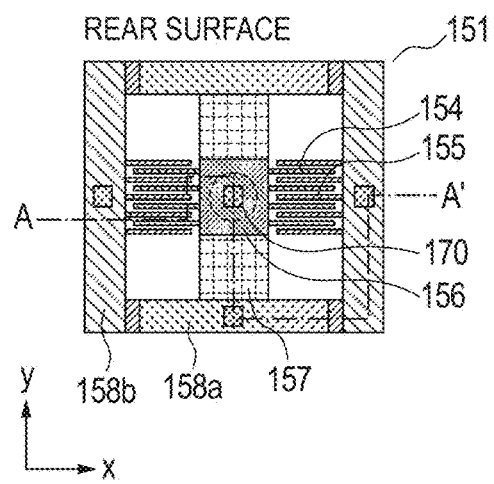
FIGS. 6A, 6B, 6C, 6D, 6E, 6F, 6G and 6H are illustrations of a first actuator of the variable shape mirror of FIG. 4A to FIG. 4C and a manufacturing method thereof.

FIG. 6A is a plan view of one first actuator in the first actuator array when seen from the rear surface side. As illustrated in FIG. 4A to FIG. 4C, the variable shape mirror includes actuator arrays each including a plurality of actuators, but only one actuator 151 is illustrated in FIG. 6A to FIG. 6H. FIG. 6B to FIG. 6H are sectional views taken along the line A-A' of FIG. 6A, and are illustrations of the method of manufacturing the structure illustrated in FIG. 6A.

The first actuator 151 includes movable comb electrodes 154, fixed comb electrodes 155, a movable portion 156, elastic bodies 157, and fixed portions 158 (158a and 158b). The movable portion 156 is coupled to the elastic bodies 157 and is connected to the movable comb electrodes 154.

Further, one end of each of the elastic bodies 157 is fixed to one of the fixed portions 158a. The movable comb electrodes 154 and the elastic bodies 157 are connected to side walls of the movable portion 156. The movable comb electrodes 154 extend in the x direction from side walls of the movable portion 156 in parallel with a y-z plane (plane perpendicular to an x axis), and the fixed comb electrodes 155 extend in the x direction from side walls of the fixed portions 158b in parallel with the y-z plane. In other words, the side walls of the movable portion 156 having the movable comb electrodes 154 provided thereon and the side walls of the fixed portions 158b having the fixed comb electrodes 155 provided thereon are opposed to each other, respectively, and thus, the movable comb electrodes 154 and the fixed comb electrodes 155 are arranged so as to be opposed to each other, respectively. Further, the electrodes are arranged so that comb electrodes thereof are alternately arrayed with a distance.

Figure 6B:
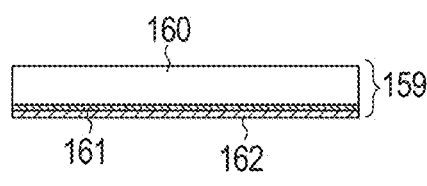

Next, a method of manufacturing the first actuator 151 is described. Here, a case in which a plurality of actuators are simultaneously formed through processing of a SOI substrate is described taking only one actuator as an example. First, as illustrated in FIG. 6B, a SOI substrate 159 including a handle layer 160, a BOX layer 161, and a silicon active layer 162 is prepared. Then, as illustrated in FIG. 6C, patterns of insulating layers 163 (163a and 163b) are formed on both surfaces of the SOI substrate 159, respectively. Specifically, after silicon oxide ($SiO_2$) formed by thermal oxidation is used to form the insulating layers 163, resist patterns (not shown) are formed, and the insulating layers 163 are etched with the resist patterns being used as masks. In etching the insulating layers 163, for example, plasma etching using tetrafluoromethane ($CF_4$), difluoromethane ($CH_2F_2$), or trifluoromethane ($CHF_3$), all of which are chlorofluorocarbon-based gases, is used. Those chlorofluorocarbon-based gases may be used alone or under a state of being mixed with another chlorofluorocarbon-based gas, or being mixed with an inert gas such as argon (Ar) or helium (He).

Figure 6F:
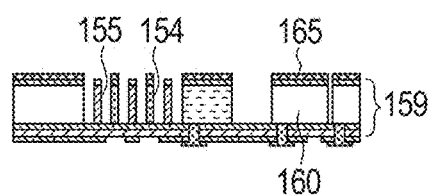
Figure 6C:
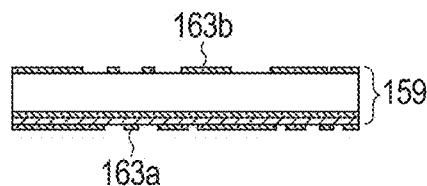
Figure 6G:
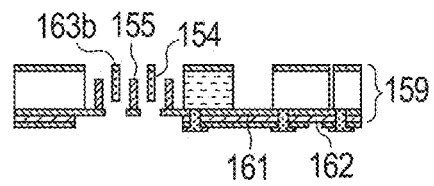
Figure 6D:
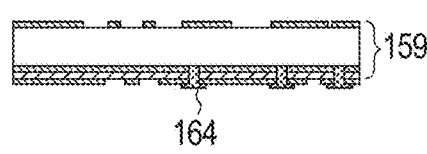

Then, as illustrated in FIG. 6D, through electrodes 164 each having a contact hole pattern are formed. First, a resist pattern (not shown) is formed on a rear surface of the SOI substrate 159. The silicon active layer 162 and the BOX layer 161 are etched to form through holes with the resist pattern being used as a mask. Further, after a chromium (Cr) film and a gold (Au) film serving as materials of the electrodes are stacked, a resist pattern (not shown) is formed. The gold (Au) film and the chromium (Cr) film are etched with the resist pattern being used as a mask.

Figure 6H:
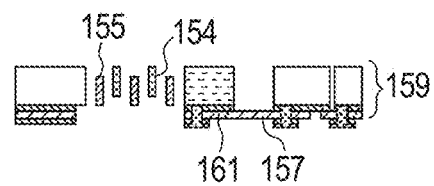
Figure 6E:
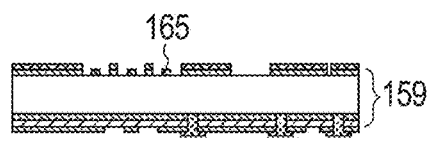

Then, as illustrated in FIG. 6E, a mask for forming the shape of the comb teeth is formed. A resist pattern 165 is formed on a surface of the SOI substrate 159 on the handle layer 160 side, and the insulating layer 163b on the surface of the handle layer 160 is etched and patterned. In etching the insulating layer 163b, plasma etching using a chlorofluorocarbon-based gas exemplified in the step illustrated in FIG. 6C is used.

Then, as illustrated in FIG. 6F, the movable comb electrodes 154 and the fixed comb electrodes 155 are formed from the handle layer 160. This is a step of etching the handle layer 160 with the resist pattern 165 formed as illustrated in FIG. 6E and the insulating layer 163b being used as masks. In this step, in order to etch the handle layer 160 to form the desired shape of the comb teeth, inductively-coupled-plasma-reactive-ion-etching (ICP-RIE) that enables etching in a direction perpendicular to the surface of the handle layer or the like is used. By using ICP-RIE, a fine comb electrode structure having a high aspect ratio can be formed.

Then, as illustrated in FIG. 6G, level differences of the movable comb electrodes 154 and the fixed comb electrodes 155 are formed. In order to adjust a level of lower surfaces of the movable comb electrodes 154 to form a level difference, the silicon active layer 162 is etched with the insulating layer (SiO$_2$) 163a on the rear surface being used as a mask. Then, the BOX layer 161 is etched with the etched and patterned silicon active layer 162 being used as a mask. Further, silicon (Si) of the movable comb electrodes 154 is etched from the rear surface side to a depth of, for example, 20 μm with the etched and patterned BOX layer 161 being used as a mask.

Further, in order to adjust a level of upper surfaces of the fixed comb electrodes 155 to form a level difference, after the resist pattern 165 on the front surface is separated, silicon (Si) of the fixed comb electrodes 155 is etched from the front surface side to a depth of, for example, 20 μm with the insulating layer (SiO$_2$) 163b on the front surface being used as a mask. In etching the silicon (Si) layer and the insulating layer, plasma etching using a chlorofluorocarbon-based gas exemplified with reference to FIG. 6C, ICP-RIE exemplified with reference to FIG. 6E, or the like is used. In those steps of forming level differences of the comb electrodes, the level of the lower surfaces of the movable comb electrodes 154 and the level of the upper surfaces of the fixed comb electrodes 155 are adjusted to form the level differences of the movable comb electrodes 154 and the fixed comb electrodes 155. In this way, in the first actuator 151, a comb electrode structure is formed in which, when a voltage is applied, a connecting portion 170 is displaced to the rear surface side of the directions perpendicular to the mirror reference plane.

Then, as illustrated in FIG. 6H, the BOX layer (SiO$_2$) 161 is etched to release the fixed comb electrodes 155 and the elastic bodies 157. In etching the BOX layer 161, for example, the BOX layer 161 is selectively wet etched using buffered hydrofluoric acid (BHF).

Note that, the actuator array and the manufacturing method thereof described above are only exemplary, and the present invention is not limited thereto. With regard to the first actuator 151, the array is, for example, a triangular lattice, and array pitches are, for example, 800 μm. In the exemplary manufacturing method described above, the first actuator is processed using a photolithography technology that can form a fine pattern. Therefore, compared with ordinary machining, the actuator can be formed more easily with higher precision.

(Method of Manufacturing Second Actuator Array)

A structure and a manufacturing method of the second actuator array 30 illustrated in FIG. 4A to FIG. 4C that is suitable for the variable shape mirror according to this embodiment are described with reference to FIG. 7A to FIG. 7H. The second actuator array 30 is also actuators of an electrostatic comb type, and is for causing displacement to, for example, the +Z direction side of the directions perpendicular to the mirror reference plane. A stroke of the displacement (maximum amount of displacement) is relatively small and is, for example, 20 μm, but there is an advantage that the amount of displacement can be finely controlled.

Figure 7A:
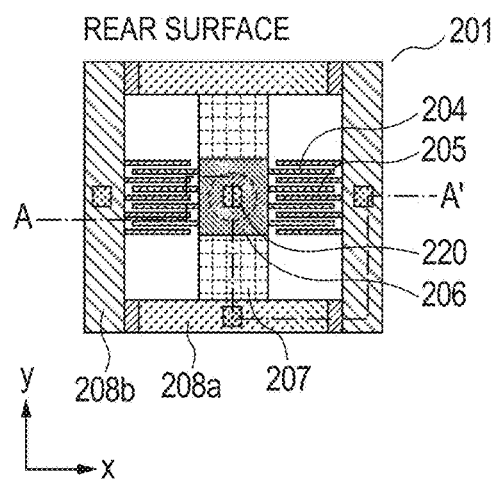
FIGS. 7A, 7B, 7C, 7D, 7E, 7F, 7G and 7H are illustrations of a second actuator of the variable shape mirror of FIG. 4A to FIG. 4C and a manufacturing method of the same.

FIG. 7A is a plan view of one second actuator in the second actuator array when seen from the rear surface side. Note that, as illustrated in FIG. 4A to FIG. 4C, the variable shape mirror includes actuator arrays each including a plurality of actuators, but only one actuator 201 is illustrated in FIG. 7A to FIG. 7H. FIG. 7B to FIG. 7H are sectional views taken along the line A-A' of FIG. 7A, and are illustrations of the method of manufacturing the structure illustrated in FIG. 7A.

The second actuator 201 is different from the first actuator 151 described with reference to FIG. 6A to FIG. 6H in level difference structures of the fixed comb electrodes and the movable comb electrodes. In the first actuator 151, as described above, in a direction approximately perpendicular to the mirror reference plane, the upper and lower surfaces of the movable comb electrode are higher (on the mirror side) than the upper and lower surfaces of the fixed comb electrode, respectively. On the other hand, in the second actuator 201, the upper and lower surfaces of the movable comb electrode are lower than the upper and lower surfaces of the fixed comb electrode, respectively.

The second actuator 201 includes movable comb electrodes 204, fixed comb electrodes 205, a movable portion 206, elastic bodies 207, and fixed portions 208 (208a and 208b). The movable portion 206 is coupled to the elastic bodies 207 and is connected to the movable comb electrodes 204. Further, one end of each of the elastic bodies 207 is fixed to one of the fixed portions 208a. The movable comb electrodes 204 and the elastic bodies 207 are connected to side walls of the movable portion 206. The movable comb electrodes 204 extend in the x direction from side walls of the movable portion 206 in parallel with a y-z plane (plane perpendicular to an x axis), and the fixed comb electrodes 205 extend in the x direction from side walls of the fixed portions 208b in parallel with the y-z plane. The side walls of the movable portion 206 having the movable comb electrodes 204 provided thereon and the side walls of the fixed portions 208b having the fixed comb electrodes 205 provided thereon are opposed to each other, respectively, and thus, the movable comb electrodes 204 and the fixed comb electrodes 205 are arranged so as to be opposed to each other, respectively. Further, the electrodes are arranged so that comb teeth thereof are alternately arrayed with a distance. The structure described above is the same as that of the first actuator 151.

Next, a method of manufacturing the second actuator 201 is described. Here, a case in which a plurality of actuators are simultaneously formed through processing of a SOI substrate is described taking only one actuator as an example. Note that, in this case, points different from those in the method of manufacturing the first actuator 151 described with reference to FIG. 6A to FIG. 6H are described, and description of the remaining points is omitted.

Figure 7B:
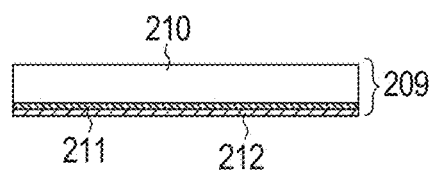

First, as illustrated in FIG. 7B, a SOI substrate 209 including a handle layer 210, a BOX layer 211, and a silicon active layer 212 is prepared. Then, as illustrated in FIG. 7C, patterns of insulating layers 213 are formed on both surfaces of the SOI substrate 209, respectively. Specifically, after silicon oxide (SiO$_2$) formed by thermal oxidation is used to form the insulating layers 213, resist patterns (not shown) are formed, and the insulating layers 213 are etched with the resist patterns being used as masks. The insulating layers 213 are etched by the same method as described with reference to FIG. 6B.

Figure 7F:
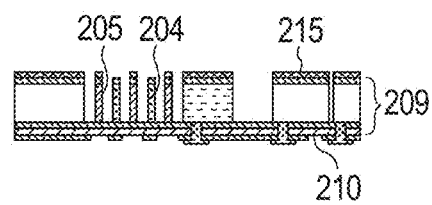
Figure 7C:
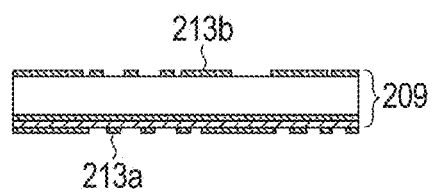
Figure 7G:
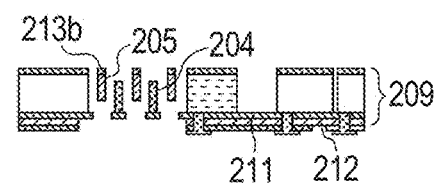
Figure 7D:
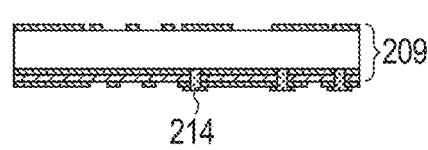

Then, as illustrated in FIG. 7D, through electrodes 214 each having a contact hole pattern are formed. First, a resist pattern (not shown) is formed on a rear surface of the SOI substrate 209. The silicon active layer 212 and the BOX layer 211 are etched to form through holes with the resist pattern being used as a mask. Further, after a chromium (Cr) film and a gold (Au) film serving as materials of the electrodes are stacked, a resist pattern (not shown) is formed. The gold (Au) film and the chromium (Cr) film are etched with the resist pattern being used as a mask.

Figure 7H:
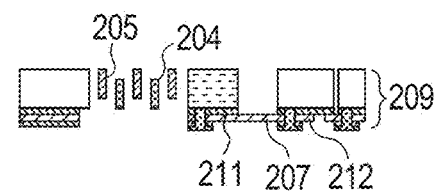
Figure 7E:
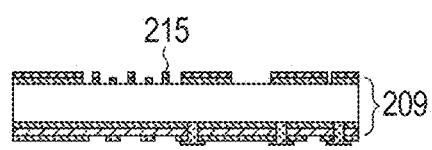
Figure 10:
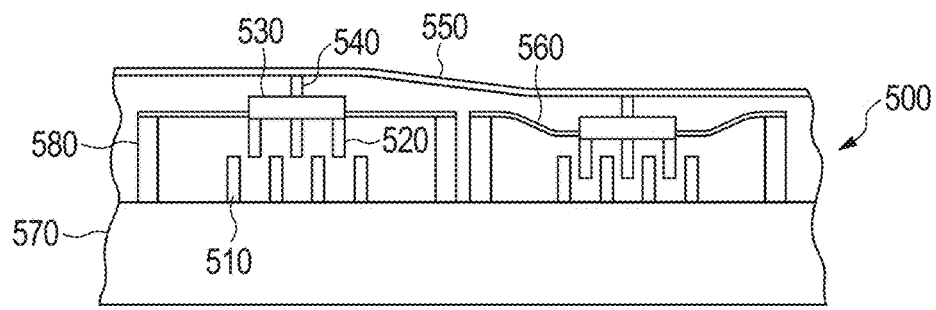
FIG. 10 is a sectional view for illustrating a related-art example.
Figure 11A:
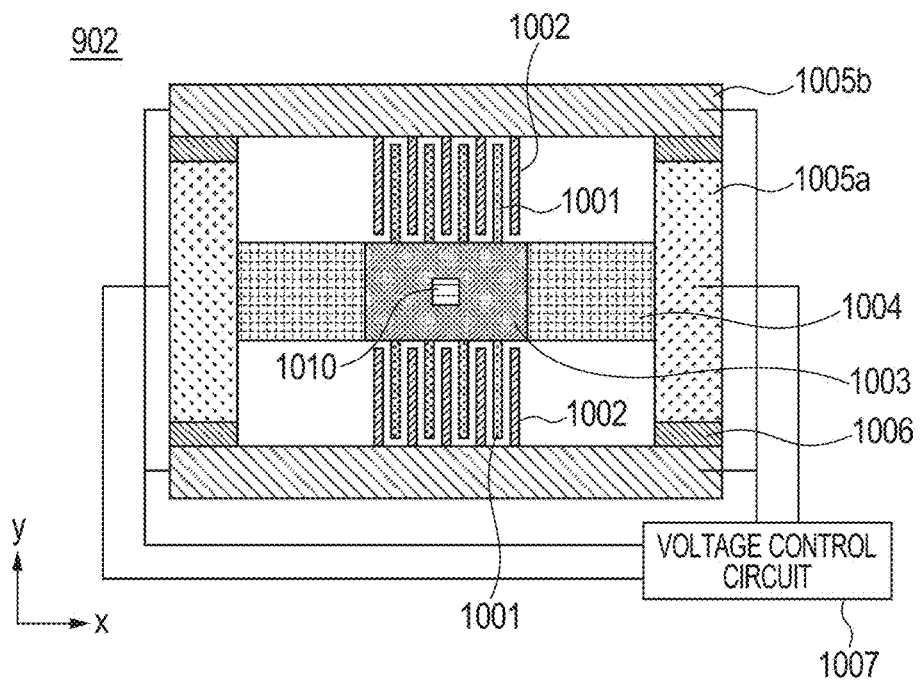
FIGS. 11A and 11B are a plan view and a sectional view for illustrating another related-art example.
Figure 11B:
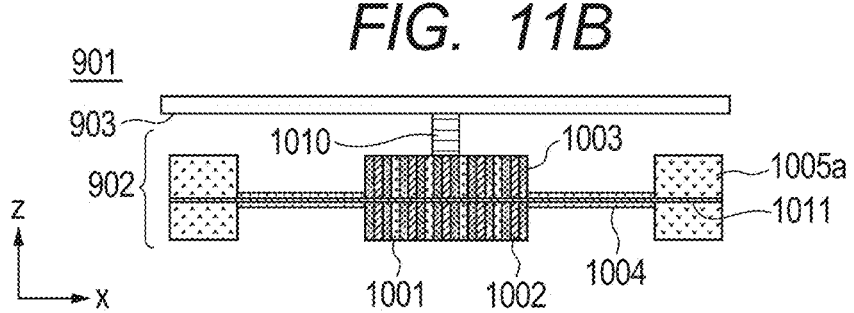

Then, as illustrated in FIG. 7E, a mask for forming the shape of the comb teeth is formed. A resist pattern 215 is formed on a surface of the SOI substrate 209 on the handle layer 210 side, and the insulating layer 213b on the surface of the handle layer 210 is etched and patterned. The insulating layer 213b is etched by the same method as described with reference to FIG. 6C.

Then, as illustrated in FIG. 7F, the movable comb electrodes 204 and the fixed comb electrodes 205 are formed from the handle layer 210. This is a step of etching the handle layer 210 with the resist pattern 215 formed as illustrated in FIG. 7E and the insulating layer 213b being used as masks. The handle layer 210 is etched to form the desired shape of the comb teeth by the same method as described with reference to FIG. 6F.

Then, as illustrated in FIG. 7G, level differences of the movable comb electrodes 204 and the fixed comb electrodes 205 are formed. In order to adjust a level of lower surfaces of the fixed comb electrodes 205 to form a level difference, the silicon active layer 212 is etched with the insulating layer ($SiO_2$) 213a on the rear surface being used as a mask. Then, the BOX layer 211 is etched with the etched and patterned silicon active layer 212 being used as a mask. Further, silicon (Si) of the fixed comb electrodes 205 is etched from the rear surface side to a depth of, for example, 20 μm with the etched and patterned BOX layer 211 being used as a mask. Further, in order to adjust a level of upper surfaces of the movable comb electrodes 204 to form a level difference, after the resist pattern 215 on the front surface is separated, silicon (Si) of the movable comb electrodes 204 is etched from the front surface side to a depth of, for example, 20 μm with the insulating layer ($SiO_2$) 213b on the front surface being used as a mask. The silicon (Si) layer and the insulating layer are etched by the same method as described with reference to FIG. 6G. In those steps of forming level differences of the comb electrodes, the level of the upper surfaces of the movable comb electrodes 204 and the level of the lower surfaces of the fixed comb electrodes 205 are adjusted to form the level differences of the movable comb electrodes 204 and the fixed comb electrodes 205. In this way, in the second actuator 201, a comb electrode structure is formed in which, when a voltage is applied, the movable portion 206 is displaced to the front surface side of the directions perpendicular to the mirror reference plane.

Then, as illustrated in FIG. 7H, the BOX layer ($SiO_2$) 211 is etched to release the movable comb electrodes 204 and the elastic bodies 207. The BOX layer 211 is etched by the same method as described with reference to FIG. 6H. The remaining points are the same as those described in the method of manufacturing the first actuator.

(Third Embodiment: Ophthalmological Apparatus)

An adaptive optics system that uses the variable shape mirror described above as a wavefront correction device that compensates for an optical aberration is described with a scanning laser ophthalmoscope (hereinafter described as "SLO apparatus") as an example. The SLO apparatus is an ophthalmological apparatus that irradiates a fundus with light so as to enable observation of a photoreceptor, a retinal nerve fiber layer, hemodynamics, or the like.

FIG. 9 is an illustration of a schematic configuration of the SLO apparatus of this embodiment. Light emitted from a light source 301 travels through a single-mode optical fiber 302 and passes through a collimator 303 to become a collimated light beam. The collimated light beam is transmitted through a beam splitter 304, which serves as a light splitting unit, as measurement light 305 to be guided to an adaptive optics system 320. The wavelength of the light source 301 for emitting, for example, laser light is not particularly limited, but particularly for fundus imaging, the wavelength of about 800 nm to 1,500 nm (for example, wavelength of 850 nm or less) is suitably used for preventing dazzling of a subject and for maintaining the resolution. The adaptive optics system 320 includes a beam splitter 306 serving as a light splitting unit, a wavefront sensor (aberration measuring unit) 315, a variable shape mirror that forms a reflective optical modulator (wavefront correction device) 308, and reflective mirrors 307-1 to 307-4 for guiding the light to those members. The respective reflective mirrors 307 are placed so that at least the pupil of the eye to be inspected, the wavefront sensor 315, and the variable shape mirror 308 have an optically conjugate relationship.

The light that has passed through the adaptive optics system 320 is scanned by a light scanning portion 309 one-dimensionally or two-dimensionally. The measurement light scanned by the light scanning portion 309 is radiated to an eye 311 to be inspected through eyepiece lenses 310-1 and 310-2. By adjusting the positions of the eyepiece lenses 310-1 and 310-2, optimum irradiation can be performed in accordance with the visibility of the eye 311 to be inspected. In this case, a lens is used in the eyepiece part, but a spherical mirror or the like may be used instead.

The measurement light radiated to the eye 311 to be inspected is reflected or scattered by a fundus (retina). The light reflected or scattered at the fundus of the eye 311 to be inspected travels, in an opposite direction, a passage similar to that during entrance, and is partially reflected by the beam splitter 306 to enter the wavefront sensor 315. Thus, the wavefront of the light beam is used for measurement. As the wavefront sensor 315, a known Shack-Hartmann sensor can be used. The reflected or scattered light that has transmitted through the beam splitter 306 is partially reflected by the beam splitter 304 to be guided to a light intensity sensor 314 through a collimator 312 and an optical fiber 313. Light that has entered the light intensity sensor 314 is converted into an electrical signal to be processed into a fundus image by an image processing unit 325.

The wavefront sensor 315 is connected to an adaptive optics controller 316 serving as a control unit to transmit the wavefront of the received light beam to the adaptive optics controller 316. The adaptive optics controller 316 is connected to the variable shape mirror 308, and the variable shape mirror 308 is deformed into a shape instructed by the adaptive optics controller 316. The adaptive optics controller 316 calculates, based on the measurement result of the wavefront obtained from the wavefront sensor 315, a mirror shape that enables correction into a wavefront with no aberration. Then, in order to reproduce the shape in the variable shape mirror 308, a necessary application voltage difference for each of the comb electrodes is calculated and sent to the variable shape mirror 308. In the variable shape mirror 308, a potential difference sent from the adaptive optics controller 316 is applied between the movable comb electrode and the fixed comb electrode, to thereby deform the mirror surface into a predetermined shape.

The measurement of the wavefront by the wavefront sensor 315, transmission of the wavefront to the adaptive optics controller 316, and instruction by the adaptive optics controller 316 to the variable shape mirror for correction of the aberration as described above are repeatedly processed to be feed-back controlled to constantly obtain an optimum wavefront. Note that, it is only necessary that the variable shape mirror that forms the reflective optical modulator is arranged so as to correct a wavefront aberration of at least one of measurement light or return light.

In the adaptive optics system according to this embodiment, the actuator of an electrostatic comb type can be displaced in the two (±) directions perpendicular to the mirror surface, and thus, adaptive optical processing can be carried out with approximately half the driven amount of the related-art variable shape mirror.

According to the one embodiment of the present invention, the variable shape mirror using the electrostatic actuator having the comb electrode structure can be realized, which can be relatively easily manufactured and, when being driven, displaced in the two (±) directions perpendicular to the mirror reference plane. As a result, for example, the mirror can be deformed into a desired shape with approximately half the driven amount of the related-art electrostatic actuator, and the residual aberration can be reduced.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-140088, filed Jul. 7, 2014, which is hereby incorporated by reference herein in its entirety.

What is claimed is:

1. A variable shape mirror, comprising:
   a mirror base including a reflective surface; and
   an actuator including a connecting portion to be connected to the mirror base, and a plurality of actuators including a first actuator and a second actuator,
   each of the plurality of actuators being connected to the mirror base via the connecting portion,
   the first actuator including a first electrode pair of a comb electrode structure, which includes a movable comb electrode and a fixed comb electrode, for displacing the connecting portion in a first direction perpendicular to the reflective surface,
   the second actuator including a second electrode pair of a comb electrode structure, which includes a movable comb electrode and a fixed comb electrode, for displacing the connecting portion in a second direction opposite to the first direction, the second electrode pair being separately formed from the first electrode pair,
   wherein each of the first actuator and the second actuator comprises:
      a movable portion leading to the connecting portion;
      the respective movable comb electrode, extending from the movable portion in a direction along the reflective surface of the mirror base;
      the respective fixed comb electrode, engaged with the movable comb electrode with a gap therebetween;
      a support portion for supporting the fixed comb electrode; and
      an elastic member connected to the support portion and the movable portion,
   wherein the movable portion of the first actuator and the movable portion of the second actuator are a same common movable portion,
   wherein in the first electrode pair, the movable comb electrode is a first movable comb electrode formed on the common movable portion, and the fixed comb electrode is a first fixed comb electrode engaged with the first movable comb electrode, and
   wherein in the second electrode pair, the movable comb electrode is a second movable comb electrode formed on the common movable portion, and the fixed comb electrode is a second fixed comb electrode engaged with the second movable comb electrode.

2. A variable shape mirror according to claim 1, further comprising a voltage application unit for applying different voltages to the respective fixed comb electrodes.

3. A variable shape mirror according to claim 1, wherein the common movable portion, the first movable comb electrode, and the second movable comb electrode are electrically at the same potential.

4. A variable shape mirror according to claim 1,
   wherein each movable comb electrode comprises a surface perpendicular to the reflective surface, the surface perpendicular to the reflective surface including a region opposed to the respective fixed comb electrode and a region not opposed to the respective fixed comb electrode,
   wherein, in the first electrode pair, the region of the first movable comb electrode, that is not opposed to the first fixed comb electrode, is formed on the mirror base side with respect to the region opposed to the first fixed comb electrode, and
   wherein, in the second electrode pair, the region of the second movable comb electrode, that is opposed to the second fixed comb electrode, is formed on the mirror base side with respect to the region not opposed to the second fixed comb electrode.

5. A variable shape mirror according to claim 1, wherein a plurality of the elastic members are equiangularly arranged about the common movable portion.

6. A variable shape mirror according to claim 1,
   wherein the first actuator includes two sets of the first electrode pairs and the second actuator includes two sets of the second electrode pairs, and
   wherein each of the two first electrode pairs and the two second electrode pairs are arranged so as to be 180° rotationally symmetric with each other with the common movable portion therebetween.

7. An adaptive optics system for correcting a wavefront aberration, comprising:
   a reflective optical modulator for correcting a wavefront aberration of incident light;
   an aberration measurement unit for measuring the wavefront aberration of the incident light; and
   a control unit for controlling the reflective optical modulator based on a result of the measurement by the aberration measurement unit,
   the reflective optical modulator comprising the variable shape mirror according to claim 1.

8. An ophthalmological apparatus for obtaining an image of an eye to be inspected, comprising:
   a reflective optical modulator for correcting a wavefront aberration of at least one of measurement light or return light;
   an aberration measurement unit for measuring an aberration caused at the eye to be inspected; and
   a control unit for controlling the reflective optical modulator based on a result of the measurement by the aberration measurement unit,
   the reflective optical modulator comprising the variable shape mirror according to claim 1.

9. A variable shape mirror, comprising:
   a mirror base including a reflective surface; and an actuator including a connecting portion to be connected to the mirror base, a first actuator, and a second actuator, each of the plurality of actuators being connected to the mirror base via the connecting portion, the first actuator including a first electrode pair of a comb electrode structure for displacing the connecting portion in a first direction perpendicular to the reflective surface, the second actuator including a second electrode pair of a comb electrode structure for displacing the connecting portion in a second direction opposite to the first direction, the second electrode pair being separately formed from the first electrode pair, wherein the first actuator and the second actuator are formed so as to be vertically shifted from each other in a direction perpendicular to the reflective surface, wherein each of the first actuator and the second actuator comprises a movable portion leading to the connecting portion, and wherein the movable portion of the first actuator comprises a first movable portion and the movable portion of the second actuator comprises a second movable portion different from the first movable portion.

10. A variable shape mirror according to claim 9,
wherein the first actuator comprises:
the first movable portion, leading to the connecting portion;
a movable comb electrode extending from the first movable portion in a direction along the reflective surface of the mirror base;
a fixed comb electrode engaged with the movable comb electrode with a gap therebetween;
a first support portion for supporting the fixed comb electrode; and
an elastic member for connecting the first support portion and the first movable portion,
wherein the second actuator comprises:
the second movable portion, leading to the connecting portion;
a movable comb electrode extending from the second movable portion in a direction along the reflective surface of the mirror base;
a fixed comb electrode engaged with the movable comb electrode with a gap therebetween;
a second support portion for supporting the fixed comb electrode; and
an elastic member for connecting the second support portion and the second movable portion,
wherein the first electrode pair comprises a pair of the first movable comb electrode formed on the first movable portion and the first fixed comb electrode engaged with the first movable comb electrode, and
wherein the second electrode pair comprises a pair of the second movable comb electrode formed on the second movable portion and the second fixed comb electrode engaged with the second movable comb electrode.

11. A variable shape mirror according to claim 10,
wherein each movable comb electrode comprises a surface perpendicular to the reflective surface, the surface perpendicular to the reflective surface including a region opposed to the respective fixed comb electrode and a region not opposed to the respective fixed comb electrode,
wherein, in the first electrode pair, the region of the first movable comb electrode, that is not opposed to the first fixed comb electrode, is formed on the mirror base side with respect to the region opposed to the first fixed comb electrode, and
wherein, in the second electrode pair, the region of the second movable comb electrode, that is opposed to the second fixed comb electrode, is formed on the mirror base side with respect to the region not opposed to the second fixed comb electrode.

12. A variable shape mirror according to claim 10, wherein a plurality of the elastic members are equiangularly arranged about an area of the first and second movable portions.

* * * * *